United States Patent [19]

Lefebvre

[11] 4,165,385

[45] Aug. 21, 1979

[54] WATER-IN-OIL EMULSION FOR SKIN MOISTURIZING

[75] Inventor: Elsa G. Lefebvre, Excelsior, Minn.

[73] Assignee: Dianis Creations, Inc., Minnetonka, Minn.

[21] Appl. No.: 596,541

[22] Filed: Jul. 16, 1975

Related U.S. Application Data

[63] Continuation of Ser. No. 364,868, May 29, 1973, abandoned.

[51] Int. Cl.² ............................................. A61K 47/00
[52] U.S. Cl. ................................................... 424/365
[58] Field of Search ............................................. 424/365

[56] References Cited

U.S. PATENT DOCUMENTS

| | | | |
|---|---|---|---|
| 2,109,842 | 1/1938 | Harris | 424/365 |
| 2,520,980 | 9/1950 | Terkel | 424/365 |
| 3,211,618 | 10/1965 | Kambersky | 424/365 |
| 3,489,690 | 1/1970 | Lachampt et al. | 424/365 X |
| 3,536,816 | 10/1970 | Kellner | 424/365 |

OTHER PUBLICATIONS

*The Cosmetic Formulary*, (1937), p. 6, Chem. Pub. Co. of N.Y. Inc., N.Y.
*Chemical Abstract*, vol. 39, (1945), 5395.
*Modern Cosmeticology*, Harry, 4th Ed., (1955), London, pp. 229–231.
*Cosmetics Science and Technology*, (1957), Interscience Pub., Inc., N.Y., pp. 87–91 & 1063–1068.

*Primary Examiner*—Frederick E. Waddell
*Attorney, Agent, or Firm*—Merchant, Gould, Smith, Edell, Welter & Schmidt

[57] ABSTRACT

A reasonably stable water-in-oil skin moisturizer cream can be prepared from up to 90 or 95 parts by weight of an oil phase containing at least 5 weight percent cocoa butter and at least 5, preferably at least 10, parts by weight of water. Borax is preferably added to the water phase. The oil phase also contains 200-400 phr vegetable oil, based on the weight of cocoa butter. Mineral oil, a suitable ester wax, and, preferably, a suitable fatty acid ester emollient are also included in the oil phase. A fatty acid amine stearate helps to stabilize the skin cream. Despite the presence of both water and cocoa butter in the same composition, storage stability problems can be overcome, and the skin cream liquifies easily on the skin.

10 Claims, No Drawings

WATER-IN-OIL EMULSION FOR SKIN MOISTURIZING

This is a continuation of my copending application Ser. No. 364,868 filed May 29, 1973 now abandoned.

FIELD OF THE INVENTION

This invention relates to water-in-oil emulsions. An aspect of this invention relates to creamy, solid, or semi-solid aqueous emulsions wherein the aqueous phase is discontinuous and the emulsion is useful as a skin cream (e.g. a face or body cream), a skin lotion, a moisturizer, or the like. An aspect of this invention further relates to moisturizing cosmetics for the skin. Still another aspect of this invention relates to a moisturizing cream or lotion having a generally continuous oily phase compatible with the oily layer of the skin, which oily phase includes entrapped water or an aqueous phase which can bring moisture to the skin.

DESCRIPTION OF THE PRIOR ART

It is a common practice, particularly in the cosmetic art, to use water-in-oil emulsions to moisturize or soften the skin or to help avoid the formation of wrinkles in the skin. Typical cosmetic formulas include oily or oleophilic materials such as ester waxes, mineral or vegetable oils, and oil-compatible emollients such as the lower alkyl esters of long-chain (preferably saturated) fatty acids. When oleophilic materials are used to make water-in-oil emulsions, such materials are generally selected for hydrolytic stability as well as their compatability with and favorable cosmetic and/or medicinal effects upon human skin. Thus, a typical practice in the art is to avoid naturally occurring triglyceride oils which have a tendency to turn rancid, e.g. in the presence of water or atmospheric moisture.

The use of olive oil in combination with distilled water in a wrinkle control cream for the skin is disclosed in a U.S. Pat. to Brown, No. 3,067,106. It is also known to use beeswax and water along with a hydrolytically-stable oil such as mineral oil in pharmaceuticals and cosmetics, as is shown by U.S. Pat. No. 3,227,616. Beeswax and triglyceride oils of various kinds have been suggested for restoring the smooth texture of the skin; see U.S. Pat. No. 3,274,063. These oils have also been used in grease paint, bath oils, and the like as well as cosmetic preparations. See, for example, U.S. Pat. Nos. 2,025,943 and 3,150,049.

One commercially available skin cream or "cold cream" which is widely used in skin care and cosmetics comprises a beeswax-borax-mineral oil emulsion with triethanolamine stearate as an auxillary emulsifier. This "cold cream" has excellent shelf life stability, since it is free of naturally occurring oils which may have a tendency to turn rancid in the presence of emulsified water.

It has long been recognized that cocoa butter (theobroma oil), which is a mixture of glycerides of saturated and unsaturated long-chain fatty acids and other naturally-occurring materials obtained by roasting, solvent-extracting, or expressing seeds of Theobroma Cacao, has particularly desirable effects upon the skin. This yellowish-white solid is soft and easily liquefied by frictional heat at room temperature. In either liquid or solid form, it is generally insoluble in water, but is compatible with a wide variety of organic (e.g. aliphatic) materials. Cocoa butter is typically used as a lubricant in massage and as a base for suppositories, ointments, toilet soaps, creams, etc. Typically, however, cocoa butter is not used in water-containing emulsions because of its tendency to turn rancid and thus detract from the shelf life of the emulsion. Several other problems are likely to be encountered in connection with the use of naturally occurring oils and the like in water-containing emulsions, e.g. thermal, freeze-thaw, and other storage stability problems (including separation due to incompatibility, etc.). A further problem is that some oily and/or water-soluble components of the emulsion can introduce an unpleasant "feel" to the cream and/or make it relatively difficult to liquefy the cream by simple application of frictional forces at room temperature, e.g. by massaging the cream onto the skin.

Accordingly, this invention contemplates providing a water-in-oil emulsion containing a significant amount of cocoa butter which, despite the presence of both water and cocoa butter in the same composition, avoids some of the prior art problems.

SUMMARY OF THE INVENTION

It has now been found that a reasonably stable water-in-oil emulsion can contain significant amounts of cocoa butter (e.g. at least about 5% by weight of the oil phase) and significant amounts of water (e.g. at least about 5% by weight of the total composition) and still provide the soothing easily liquefiable properties of cocoa butter. (In this context, the term "easily liquefiable" means that a thin film of the emulsion on the skin liquefies easily when friction and pressure are applied, e.g. by massaging the emulsion into the skin.) It is a feature of an emulsion of this invention that the oleophobic or "oil" phase contains both vegetable oil and cocoa butter in a ratio of at least 2:1 and even as high as 4:1. Mineral oil, a suitable ester wax, and, preferably, a suitable emollient (e.g. of the fatty acid ester type) are also contained in the oil phase. The amount of water in the emulsion, though constituting at least about 5% and preferably at least about 10% of the total composition, is generally less than the amount of liquid vegetable oil in the "oil" phase. It is preferred to include borax in the water phase and to take advantage of the micelle-forming properties of the amine salts of long-chain fatty acids to help stabilize the emulsion.

The significant, but relatively small amount of water (as compared to the total "oil" phase) and the relative proportions of materials in the "oil" phase (e.g. the high vegetable oil-to-cocoa butter ratio) appear to contribute in some fashion to the stability and the desirable properties of this invention. The manner in which the components of the emulsion cooperate is not fully understood, and, in any event, this invention is not bound by any theory. It is theorized that the amount of mineral oil and ester wax, though relatively small, combined with the large amount of vegetable oil in the "oil" phase contribute in some manner to the hydrolytic stability of the cocoa butter without significantly detracting from or diluting the desirable properties of the cocoa butter. For example, it may be that the cocoa butter has a tendency to be relatively more isolated from the water/oil interface in the emulsion than might otherwise be expected.

Definitions

The terms "oil phase", "water phase", "water-in-oil emulsion", "long-chain fatty acid", and other terms used herein have a well-recognized meaning in the art.

For purposes of greater clarity, however, these terms are specifically defined as follows:

"Oil phase" refers to the phase of an emulsion which comprises oleophilic or lipophilic and generally hydrophobic ingredients. Thus, an "oil" phase can include triglyceride oils, paraffins, waxes, fatty acids and fatty acid derivatives, and other organic, relatively non-polar liquid or solid ingredients.

The "water" or "aqueous" phase refers to the water itself and hydrophilic and surfactant materials dissolved or dispersed in the water. Micelle-forming surfactant materials are, of course, typically concentrated near the oil/water interfaces of the emulsion.

"Water-in-oil" emulsions are those wherein the "water phase" is discontinuous and is dispersed throughout the "oil" phase, which is continuous.

"Long-chain fatty acids" are typically those carboxylic acids containing at least 12 carbon atoms. Although naturally occurring fatty acids containing as many as 26 carbon atoms can be obtained from common sources (e.g. beeswax), amine salts and emollient esters used in this invention are typically derived from $C_{12}$–$C_{22}$ fatty acids, preferably saturated, e.g. lauric, myristic, palmitic, and stearic acids.

DETAILED DESCRIPTION

Water-in-oil emulsions of this invention comprise a major amount of an oil phase and a minor amount of a water phase. Although suitable formulations of this invention can be in the form of viscous liquids, soft solid emulsions are preferred.

The cocoa butter is a key ingredient of the oil phase and provides a convenient reference point for amounts of other oil phase components. Thus, the amount of liquid vegetable oil is ordinarily 200-400 parts by weight per 100 parts by weight of cocoa butter. The amount of ester wax is generally in the range of 25-100 parts by weight; the amount of mineral oil is also about 25-100 parts by weight; and the amount of emollient can be up to 100 parts by weight; all of the above amounts being on the basis of parts per 100 (phr) by weight of cocoa butter.

Unless otherwise indicated, all amounts of ingredients of this invention are expressed in parts by weight or weight %. As pointed out previously, a particularly useful expression of amounts of ingredients is in parts per hundred (phr) of cocoa butter.

The aqueous phase of an emulsion of this invention comprises at least 80% by weight of water. It is greatly preferred to include 0.1-2% by weight of borax in the aqueous phase. One of the preferred surfactants for stabilizing the emulsion is an amine salt of a long-chain fatty acid, e.g. triethanolamine stearate. The micelle-forming capabilities of the amine salt may further assist in forming a barrier zone between the cocoa butter in the oil phase and the water of the aqueous phase. In any event, the amine salt surfactant will typically be concentrated near the oil/water interfaces of the emulsion.

Although a significant amount of water is present in the emulsion as a discontinuous phase, the weight of the oil phase is generally 2-5 times the weight of the aqueous phase. Ordinarily, the largest component of the composition is the vegetable oil of the oil phase, which makes up about 30-50% by weight of the total composition. Among the other relatively large components of the composition are the water, cocoa butter, and ester wax, which generally comprise about 15 to about 25 weight percent, about 5 to about 25 weight percent, and about 3 to about 15 weight percent of the total composition, respectively.

A typical general formulation for an emulsion of this invention containing 5-25% by weight of cocoa butter is as follows:

| Amount (Based on 100 parts by weight cocoa butter) | Ingredient |
| --- | --- |
| 275–350 | Vegetable oil (e.g. safflower oil) |
| 40–80 | Naturally occurring ester wax (e.g. beeswax) |
| 40–80 | Emollient (e.g. isopropyl myristate) |
| 40–80 | Mineral oil |
| 0–5 | Oil-compatible preservatives, stabilizers, surface active agents, anti-oxidants, etc. |
| 125–200 | De-ionized or distilled water |
| 1–5 | Borax |
| 1–5 | Amine salt surfactant (e.g. triethanolamine stearate) |
| 0–10 | Water-compatible additives such as preservatives, inorganic suspending agents, and the like |

As is known in the art, perfume and coloring matter can be added to the emulsion. As a general rule, the total amount of perfume and coloring (e.g. a vegetable coloring) will amount to less than 1% of the total composition.

In the foregoing description of a typical formula, the ingredients have been described in more or less general terms. All materials within these generic classes of materials do not work with equal effectiveness, and certain materials are particularly preferred, as will become clear from the following description of ingredients. Unless otherwise indicated, pure or purified ingredients are preferred, e.g. ingredients meeting U.S.P. standards. It is particularly important to use a purified grade of cocoa butter.

The Oil Phase

As pointed out previously, key ingredients of the oil phase are the cocoa butter, the vegetable oil, the ester wax, the mineral oil, and various oil-compatible additives.

The preferred vegetable oil is an edible grade of safflower oil. Safflower oil is a drying oil derived from safflower (carthamus) seed and has properties somewhat similar to linseed oil. It is rich in unsaturated fatty acids such as linoleic acid. Other edible liquid triglycerides such as corn oil, soya oil, cottonseed oil, and the like can be substituted for safflower oil, but are not preferred. These oils vary in composition depending upon season, geographic location, climate, and other uncontrollable factors, but safflower oil appears to provide a well-controlled product with good properties.

Of the various naturally-occurring and synthetic ester waxes (which are typically long-chain fatty acid esters of long-chain fatty alcohols), beeswax is greatly preferred and is generally recognized as safe for use in pharmaceuticals and cosmetics. It has been found that beeswax does not detract from the ease of liquefying emulsions of this invention.

Although a variety of amine salt emulsifiers can be derived from tertiary amines and $C_{12}$–$C_{22}$ fatty acids, the preferred amine salt surfactant used in emulsions of this invention is derived from triethanolamine and a long-chain saturated fatty acid such as stearic acid. As is known in the art, triethanolamine salt of fatty acids can be formed and then blended with the emulsion or can be formed in situ by adding the fatty acid to the oil phase and the triethanolamine to the water phase, the amine salt being formed when the oil and water phases are blended together and the emulsion is formed.

Esters of lower alkanols and $C_{12}$–$C_{22}$ fatty acids are known to have emollient effects. All emollients in this class are not equally compatible with oleophilic materials, however, and isopropyl myristate is the preferred emollient.

To improve the "feel" of the composition, surface active agents such as the polyoxyethylene sorbitols can be included by adding them to the oil or water phase (typically to the oil phase). Thee agents help provide a pleasing smooth sensation when the user's fingers come in contact with the soft solid emulsion. Another useful additive for the oil phase is an oil-compatible preservative such a propyl para-hydroxybenzoate. Antioxidants such as butylated hydroxy toluene can be included to protect against oxidation of the oil phase ingredients.

The Water Phase

The principal component of the aqueous phase, generally at least in the amount of 80%, is deionized or distilled water. The borax (sodium tetraborate decahydrate) can be dissolved in the water. As pointed out previously, a common practice useful in this invention is to also dissolve triethanolamine in the water phase, so that the amine salt surfactant can be formed in situ when the water and oil phases are combined. It can be desirable to add a water-compatible preservative to the water phase to supplement the oil-compatible preservative in the oil phase. For example, methyl para-hydroxy benzoate has a much higher water solubility than the corresponding propanol ester analog and can be readily dissolved or dispersed in a water phase. According to published data, up to 1 gram of methyl para-hydroxybenzoate will dissolve in as little as 400 milliliters of water.

It has been found that water-compatible inorganic suspending agents of the silicate type (e.g. magnesium aluminum silicate suspending agents) help to preserve the overall stability of the composition when included in the water phase.

Methods of Manufacture

As is known in the art, it is possible to combine all the oil phase ingredients first, combine the water ingredients in a separate container, add the water phase to the oil phase with heat and agitation, reduce the size of the resulting emulsified water droplets with a colloid mill or the like, and then add perfume, if desired. Coloring matter, if used, can be added after the oil and water phases have been combined (before or after colloid milling) or at any other suitable time. Solid oil phase components such as ester waxes, stearic acid, and the like can be melted to provide a molten oil phase which will readily take up cocoa butter, vegetable oil, emollients, mineral oil, and the like.

An alternative method is to pre-emulsify one or more components of the composition and combine the pre-emulsion with an oil phase or a water phase. For example, some or all of the beeswax, mineral oil, emollient, and the like can be combined in a pre-emulsion with water, with the assistance of triethanolamine stearate as a surfactant or emulsifying agent. The resulting pre-emulsion can then be combined with an oil phase comprising the cocoa butter, vegetable oil, and some or all of the beeswax.

Both of these mixing techniques are illustrated in the Examples which follow, wherein all parts are by weight unless otherwise specified.

EXAMPLE 1

| Part A - Oil Phase | |
|---|---|
| Parts | Ingredient |
| 100 | Cocoa butter |
| 300 | Safflower oil |
| 50 | Beeswax |

| Part B - Pre-Emulsion | |
|---|---|
| Parts | Ingredient |
| 16.5 | Water |
| 12.5 | Beeswax |
| 2.5 | borax |
| 65 | Mineral oil |
| 2.5 | Triethanolamine stearate |
| 60 | Isopropyl pyristate |
| 2.5 | Preservatives |

Method: Part B was pre-emulsified and the resulting emulsion was added to Part A with stirring. Perfume and coloring were added to the resulting product which was a soft solid.

EXAMPLE 2

This Example illustrates the use of a method wherein the water and oil phases are directly combined. In this Example, the amounts of safflower oil, beeswax, isopropyl myristate and mineral oil, based on the amount of cocoa butter, are 333 phr, 62.5 phr, 58.3 phr, and 66.7 phr, respectively.

In the formulas for the oil phase and water phase which follow, the number of parts used are converted to weight percent (of the total emulsion) to better illustrate the relative size of the various components.

Oil Phase

| Parts | Wt. % | |
|---|---|---|
| 192 | 12.0 | Purified cocoa butter (Hershey's cosmetic grade U.S.P.) |
| 640 | 40.0 | Safflower oil, edible |
| 120 | 7.5 | Beeswax, U.S.P. |
| 112 | 7.0 | Isopropyl myristate, U.S.P. |
| 128 | 8.0 | Mineral oil |
| 37 | 2.3 | Stearic acid, U.S.P. |
| 13 | 0.8 | "Tween" 60 (trademark for polyoxyethylene sorbitan monostearate surfactant) |
| 2 | 0.1 | "Propyl Paraben" (trademark for propyl p-hydroxy benzoate) |
| 0 | 0.05 | "Tenox" 2 (antioxidant) |

Water Phase

| Parts | Wt. % | |
|---|---|---|
| 315 | 19.7 | Deionized water |
| 3 | 0.2 | "Methyl Paraben" (trademark for methyl para-hydroxyl benzoate) |
| 5 | 0.3 | "Veegum" regular (trademark for inorganic suspending agent) |
| 4.5 | 0.3 | Borax |
| 18 | 1.1 | Triethanolamine, U.S.P. |

Additives

| Parts | Wt. % | |
|---|---|---|
| 10 | 0.6 | Perfume ("Noville" #16581) |
| 0.01 | — | Food, Drug & Cosmetic Red #2 coloring |

Method:
(1) The deionized water was heated to 160° F., and the "Methyl Paraben" was dispersed in the hot water. The "Veegum" was then added and mixed with high speed agitation until thoroughly dispersed.
(2) The borax and triethanolamine were added to the water dispersion, and the resulting dispersion was heated to 170° F.
(3) The beeswax and stearic acid were melted in separate kettle.
(4) The cocoa butter, safflower oil, isopropyl myristate, mineral oil, "Tween 60", "Propyl Paraben", and "Tenox 2" were added to the molten phase of step (3), and the resulting mixture was heated to 170° F. with mixing.
(5) The water phase was added to the oil phase at 170° F.
(6) The two phases were mixed with vigorous agitation to obtain a good emulsion.
(7) The color, dissolved in a small amount of water, was added to the emulsion.
(8) The colored emulsion was passed through an Eppenbach colloid mill into the cooling kettle. A gap setting of 0.010 inches was used. Cooling water was circulated in the mill during this step.
(9) The milled emulsion was cooled with moderate agitation to 115° F., and the perfume was then added.
(10) The cooling was continued with slow mixing to 108°–110° F.

The product can be packaged in glass or plastic jars.
The following ingredients, identified above solely or primarily by trademark, can be more particularly described as follows:

"Tween" 60; polyoxyethylene (20) sorbitan monostearate having an acid number of 0–2.0, a saponification number of 45–55, a hydroxyl number of 81–96, and an average oxyethylene content of 20 oxyethylene units per sorbitan nucleus.

"Tenox" 2; an anti-oxidant consisting of 20 weight percent butylated hydroxyanisole, 6 weight percent propylgalate, 4 weight-percent citric acid, and 70 weight-percent propylene glycol.

"Veegum" is a complex colloidal form of magnesium aluminum silicate refined from naturally occurring minerals. It forms a hydrophilic colloid in water. This silicate is refined so as to meet specifications of solubility, viscosity, moisture content, pH, bacterial count, and contaminant content (i.e. arsenic and lead), the specifications being set by C.T.F.A. (Cosmetic, Toiletry, and Fragrance Association) issued Apr. 24, 1961, and revised on June 8, 1962, Feb. 10, 1065, and May 30, 1971 (formerly T.G.A. specification number 82). The specifications are set according to U.S.P. and C.T.F.A. methods, so as to be reproduceable. Test methods and specifications are available from the R. T. Vanderbilt Company, Inc., of Norwalk, Connecticut, and from the C.T.G.A. in Washington, D.C.

What is claimed is:

1. A water-in-oil emulsion comprising water dispersed in an oil phase comprising the following ingredients:
   purified cocoa butter,
   a liquid triglyceride vegetable oil,
   a $C_{12}$–$C_{26}$ fatty acid ester wax, and mineral oil;
   the amounts of said ingredients being defined as follows:

| % by Weight of Total Composition | Parts by Weight per 100 Parts by Weight of Cocoa Butter | Ingredient |
|---|---|---|
| 5–25 | — | cocoa butter |
| 30–50 | 200–400 | vegetable oil |
| 3–15 | 25–100 | ester wax |
| Same as wax | 25–100 | mineral oil |
| 5–25 | | water |

2. The emulsion of claim 1 wherein said oil phase further comprises up to 100 parts, per 100 parts by weight of said cocoa butter, of isopropyl myristate.

3. The emulsion of claim 2 wherein said emulsion is a soft solid, and wherein said oil phase comprises, per 100 parts by weight of cocoa butter:
   275–300 parts by weight of said vegetable oil
   40–80 parts by weight of said ester wax
   40–80 parts by weight of mineral oil
   125–200 parts by weight of water.

4. The emulsion of claim 2 wherein said water is contained in an aqueous phase comprising at least 80% by weight of water, 0.1–2% by weight of borax, and, at least at the surfaces thereof, 1–10% by weight of triethanolamine stearate.

5. The emulsion of claim 2 wherein said oil phase comprises at least 25 parts by weight of isopropyl myristate.

6. The emulsion of claim 2 wherein said emulsion is a soft solid.

7. The emulsion of claim 2 wherein said oil phase comprises, per 100 parts by weight of said cocoa butter:
   275–350 parts by weight safflower oil,
   40–80 parts by weight beeswax,
   40–80 parts by weight isopropyl myristate, and
   40–80 parts by weight mineral oil, and wherein the total weight of said oil phase is 2–5 times the weight of said aqueous phase.

8. The emulsion of claim 2 wherein the amount of water is 125–200 parts by weight per 100 parts by weight of said cocoa butter, based on the total weight of the emulsion.

9. A water-in-oil emulsion according to claim 1 consisting essentially of, by weight, the following ingredients in approximately the indicated amounts:
   12% purified cocoa butter, U.S.P.;
   40% edible safflower oil;

7% isopropyl myristate, U.S.P.;
8% mineral oil; and
20% water.

10. A soft, solid water-in-oil emulsion according to claim 1 consisting of water dispersed in an oil phase, said oil phase consisting of:

| Weight % | Ingredient |
|---|---|
| 12.0 | purified cocoa butter, U.S.P. cosmetic grade |
| 40.0 | edible safflower oil |
| 7.5 | beeswax, U.S.P. |
| 7.0 | isopropyl myristate, U.S.P. |
| 8.0 | mineral oil |
| 2.3 | stearic acid, U.S.P. |
| 0.8 | polyoxyethylene sorbitan monostearate with an acid number of 0–2.0, a saponification number of 45–55, a hydroxyl number of 81–96, and an average oxyethylene content of 20 oxyethylene units per sorbitan nucleus |
| 0.1 | propyl p-hydroxy benzoate |
| 0.05 | of an anti-oxidant consisting of 20 weight-% butylated hydroxyanisole, 6 weight-% propyl gallate, 4 weight-% citric acid, and 70 weight-% propylene glycol | said water phase consisting of:

| Weight % | Ingredient |
|---|---|
| 19.7 | deionized water |
| 0.2 | methyl-p-hydroxybenzoate |
| 0.3 | colloidal complex of magnesium aluminum silicate, C.T.F.A. specification of April 24, 1961, revised June 8, 1962, February 10, 1965, and May 30, 1971, formerly T.G.A. specification no. 82 |
| 0.3 | borax |
| 1.1 | triethanolamine, U.S.P. |
| 0.6 | perfume and a coloring agent. |

* * * * *

UNITED STATES PATENT AND TRADEMARK OFFICE
CERTIFICATE OF CORRECTION

PATENT NO. : 4,165,385
DATED : August 21, 1979
INVENTOR(S) : Elsa G. Lefebvre

It is certified that error appears in the above-identified patent and that said Letters Patent are hereby corrected as shown below:

Column 1, line 18, for "oily layer" read --oily outer layer--.
Column 5, line 22, for "Thee" read --These--.
Column 6, line 28, for "borax" read --Borax--.
Column 6, line 31, for "pyristate" read --myristate--.
Column 6, line 67, for "0" read --0.8--.

Signed and Sealed this

Twenty-ninth Day of April 1980

[SEAL]

Attest:

SIDNEY A. DIAMOND

Attesting Officer

Commissioner of Patents and Trademarks